United States Patent [19]

Hessberg et al.

[11] 4,300,554
[45] Nov. 17, 1981

[54] PORTABLE INFUSION APPARATUS

[75] Inventors: Sigfried Hessberg, Melsungen; Werner Dold, Triberg, both of Fed. Rep. of Germany

[73] Assignee: Intermedicat GmbH, Emmenbrucke, Switzerland

[21] Appl. No.: 121,494

[22] Filed: Feb. 14, 1980

[30] Foreign Application Priority Data

Feb. 22, 1979 [DE] Fed. Rep. of Germany ....... 2906830

[51] Int. Cl.³ .............................................. A61M 5/00
[52] U.S. Cl. ........................ 128/218 A; 128/DIG. 12
[58] Field of Search ........... 128/218 A, 218 R, 218 P, 128/218 PA, 218 F, 234, 236, 215, DIG. 1, 214 F, DIG. 12

[56] References Cited

U.S. PATENT DOCUMENTS

| | | | |
|---|---|---|---|
| 2,602,446 | 7/1952 | Glass et al. | 128/218 A |
| 2,896,621 | 7/1959 | Rodrigues | 128/218 A |
| 3,415,419 | 12/1968 | Jewett et al. | 128/218 A X |
| 3,886,938 | 6/1975 | Szabo et al. | 128/218 A |
| 4,059,110 | 11/1977 | Wuthrich et al. | 128/218 A |

*Primary Examiner*—John D. Yasko
*Attorney, Agent, or Firm*—Merriam, Marshall & Bicknell

[57] ABSTRACT

Disclosed is a portable continuous infusion apparatus for administering an injectable liquid to a patient. The apparatus expels the contents of a syringe on a time controlled basis. It employs two separate springs, with one spring used to power a clockwork and another spring to power a gear rack to advance the syringe plunger or piston. Opening and shutting the apparatus cover automatically winds both springs simultaneously. A safety prevents closing the cover unless the springs are wound. Advancement of the gear rack is adjustable by a control which acts on an escapement lever which regulates an escape wheel. The control moves the escapement lever axially so it can engage a different number of wings on the escape wheel, thereby regulating the incremental advance of the gear rack acting on the syringe plunger.

17 Claims, 9 Drawing Figures

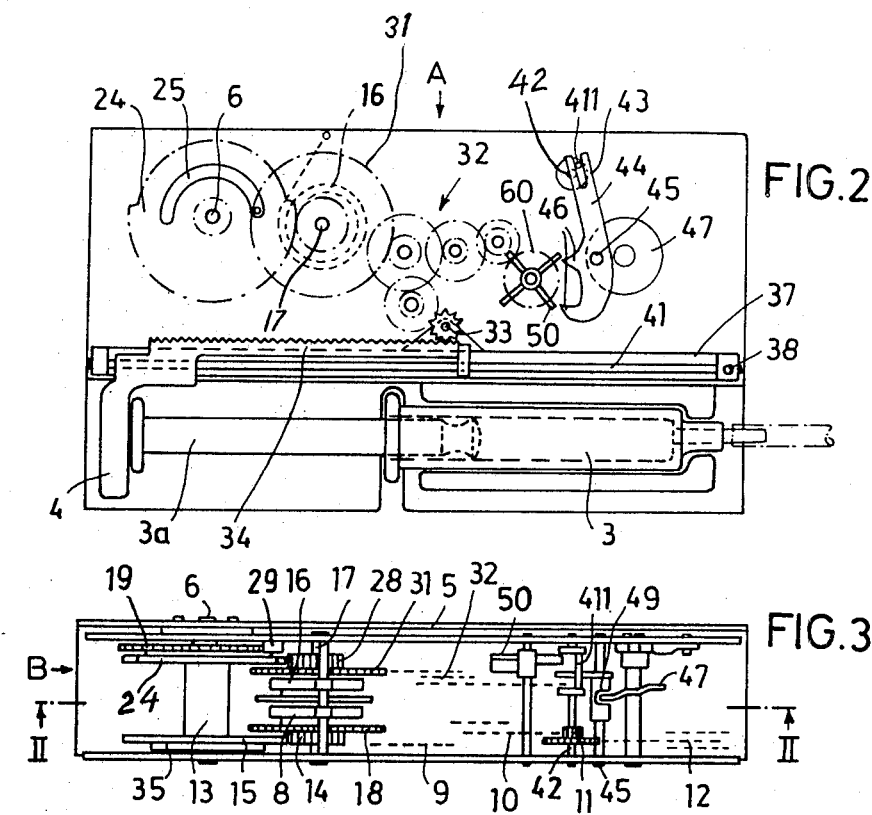
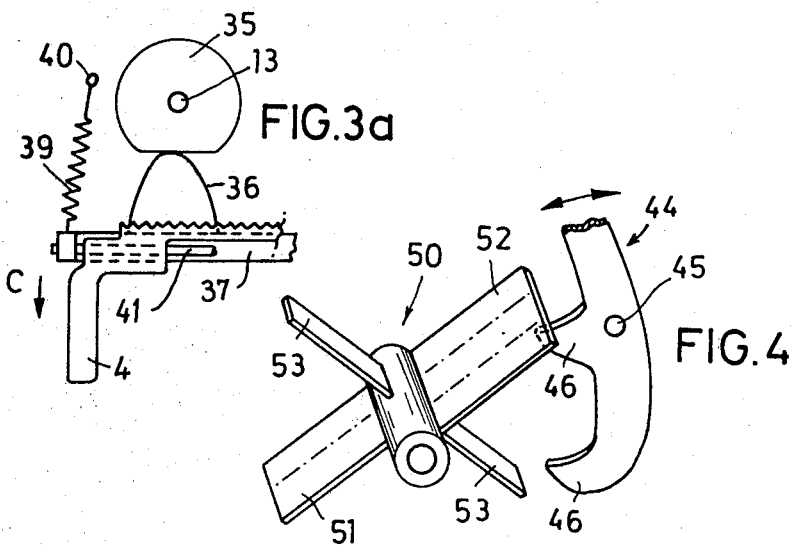

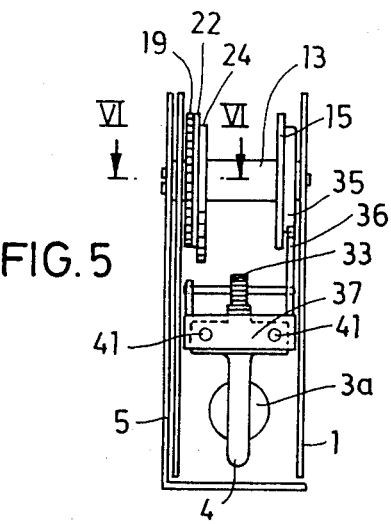
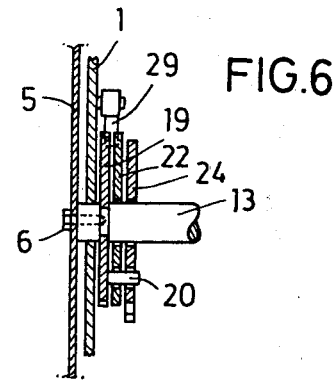
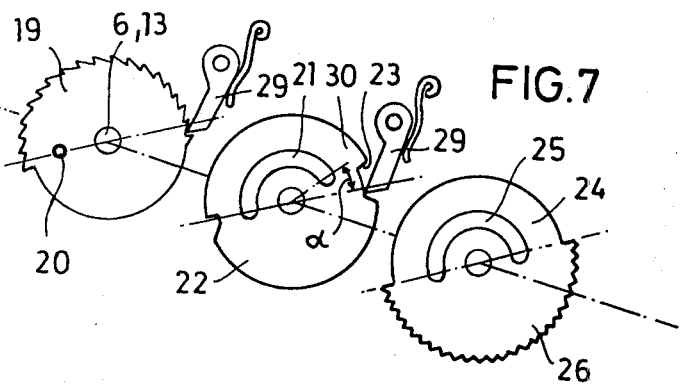
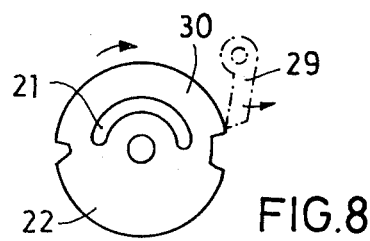

PORTABLE INFUSION APPARATUS

This invention relates to continuous infusion apparatus having a mechanism for forcing a fluid out of a syringe, and particularly such a mechanism which is spring actuated to advance a syringe piston or plunger and a mechanical clockwork or timer to regulate the rate of piston advance.

In the treatment of many sicknesses, it is necessary to continuously administer into a patient's bloodstream small doses of highly effective chemical substances naturally present in the body, as well as medicines, over an extended period of time. For this purpose, a small container housing a syringe is fastened to a patient's body. The syringe is actuated by means of a gear drive to effect continuous injection or infusion. Such a mechanism has been operated by a battery powered electric motor. The mechanism includes a screw containing a nut rotated by a gear. Linear movement of the nut is transferred to the syringe piston thereby forcing liquid out of the syringe. No timer or clockwork is incorporated into the mechanism. Flow of the liquid is effected by the gearing so a separate container housing design is needed for each different infusion feed rate. Regulating the dosage rate requires that the flowability of the liquid infusion or injection medium be carefully standardized.

The described mechanism reliability is dependent on the charge condition of the battery. If there is an unexpected battery failure the liquid injection stops immediately. While the mechanism could be adapted for connection to an electrical supply outlet in a building to eliminate the insecurity inherent with use of a battery, this would require that the patient stay at the site for the entire injection time period. Furthermore, it has been established that introduction of any electricity into a patient, even of microampere amount, causes heart problems.

To avoid the disadvantages associated with an electric drive, a spring powered drive gear has been proposed according to U.S. Pat. No. 3,886,938 for actuating an injection syringe for effecting a continuous infusion into a patient. The spring powered mechanism advances the syringe piston while the liquid feed is controlled by a mechanical timer or clockwork. This mechanism has a gear rack connected to the syringe piston and uses a helical or spiral spring to pull the gear rack forward to push the syringe piston to cause the liquid to flow out of the syringe discharge end. Advance of the gear rack is controlled by a mechanical clockwork engaged with a pinion gear meshed with the gear rack. This fully mechanical apparatus avoids the disadvantages connected with an electric powered drive but it involves problems of its own. Specifically, the helical spring fatigues with use and its capability to apply force drops uncontrollably. This may show up in inaccuracies of the clockwork control because the pinion gear transmits propulsive force from the clockwork spring to the gear rack. Also, the mechanism lacks means for adjusting the propulsive force of the helical spring, or adjusting the clockwork control, to varying degrees of sliding resistance, or friction, between the syringe piston and the syringe cylinder wall. To prevent syringes having pistons or plungers with different sliding resistance from causing inaccurate infusion, it would be necessary to use syringes having pistons or plungers with completely identical sliding resistance, but this would be impractical and probably impossible. Furthermore, the apparatus has only one operating speed. A drive unit with different spring equipment is required for each separate infusion rate. In addition, since the winding mechanism of the clockwork is used to bias the helical springs a safety is lacking which would make sure that the helical springs are biased sufficiently so that their adjustment length is sufficient for them to cause complete expulsion of the infusion liquid from the syringe.

The subject invention is concerned with the problem of providing a mechanical drive mechanism for a continuous infusion syringe which will uniformly advance a syringe piston or plunger regardless of the varying sliding resistance of these elements between different syringes, which will be adjustable to vary syringe plunger advancing speeds and which can be operated in a simple and dependable manner.

According to the invention, it is proposed to solve the described problem in continuous infusion apparatus by using separate and independent kinetic actions or forces to power the clockwork and to propel the syringe plunger or piston. A first coil spring and a wheel or gear mechanism drives the clockwork, and a second coil spring and wheel mechanism propels the syringe plunger. Each drive mechanism is independently operative of the other so that uniform clockwork movement, and uniform propulsion of the syringe piston, is achieved. Any non-uniform sliding resistance between the pistons and cylinders of individual syringes is rendered inconsequential when the mechanism of the invention is used. Also, the mechanism can be used to completely empty different kinds of syringes with the same accuracy during a desired time period. The windable coil springs used in the mechanism can operate for many years with practically unchanged spring characteristics and the spring force transmitted via the wheel or gear mechanism to the syringe piston remains essentially constant. The coil tension spring of the clockwork mechanism operates the clockwork exclusively and it applies no propulsive force to the syringe piston. This results in a very accurate clockwork control which, in turn, results in uniform advance of the syringe piston or plunger.

Both coil springs are advantageously mounted coaxially on one shaft and are desirably connected to one common winding shaft. With such an arrangement, both coil springs are always wound simultaneously and neither one of them will be overlooked and left unwound. A key can be used to wind the coil springs. However, it is advantageous to connect a pivotal cover to a spring winding shaft in a housing containing the syringe drive gear and the clockwork. The housing contains a syringe support space which the cover closes. Access to the syringe support space is obtained by pivoting the cover out of the way. Rotatable movement of the cover winds both coil springs. So that the user will always wind both coil springs completely, a safety is provided against premature closing of the cover. The safety consists of a partly toothed helical disk, fixedly connected to the cover, which so coacts with a spring ratchet that the cover can be locked only after first pivoting it 180° from the closed position. Thus, the cover can be closed only when the liquid infusion feed mechanism and the clockwork are wound completely by being tensioned or biased completely to 180°. A cam surface actuated by an entrainment pin on the helical disk is used to lock the spring ratchet in a terminal pivotal position. The cover can be opened at any time to remove the syringe at will from the syringe support in the housing, and even before the end of the total infusion time.

An eccentric pivots an escapement lever acting on an escape wheel which controls movement of a sprocket which, by means of a transmission, drives a pinion gear which advances a gear rack. The gear rack has an arm which operatively contacts the end of a syringe piston or plunger. The eccentric is located on the same shaft as the second (time) wheel of the clockwork. This mechanical arrangement permits transmission of the time control function from the clockwork to the mechanism driving or advancing the syringe piston or plunger. The simple design assures dependable operation of the time control. The escapement lever temporarily blocks the feed mechanism gear movement by acting on the escape wheel and momentarily preventing its rotation. However, the continuing rotation of the clockwork second (time) wheel or gear causes the escapement lever to disengage from the escape wheel so that the escape wheel can turn again. As the escape wheel turns, by means of a sprocket and transmission, it drives a pinion gear meshed with the gear rack. Releasing of the blocked escape wheel can be effected as frequently as is desired per unit of time to exert force or feed thrusts on the pinion gear of the syringe piston feed or advancement mechanism. By the design of the escapement lever and the escape wheel it is possible to control different kinetic cycles. A uniform and gradual expulsion of the syringe liquid content results in each case, regardless of the viscosity of the preparation to be injected and the sliding resistance of the piston or plunger in the syringe cylinder.

The escapement lever can be provided with two tandem stop dogs for engaging the escape wheel. The escape wheel can be appropriately designed like an impeller or paddle wheel with symmetrically arranged radially positioned wings or paddles. The width of the wings can vary, one from the other so that, advantageously, the escapement lever can selectively block rotation of the escape wheel by adjustable axial displacement of the escapement lever, on a shaft, relative to the escape wheel wings. As a result, the syringe piston can be advanced with different speeds. The clockwork is not effected by this control and always unwinds with the same running time. In order to obtain long infusion times, the escapement lever is set to block as many escape wheel wings as possible per unit of time so that the advancing movement of the syringe piston is divided into short distance increments, thereby extending the total feed time. Reducing the total feed time is effected by increasing the increments with which the syringe piston is advanced. Increasing the increments is effected by having the escapement lever engage per unit of time, a smaller number of escape wheel wings in order to stop the escape wheel less frequently per unit of time.

A cam in the form of a disk with undulated sides which engages a transverse slot in the shaft holding the escapement lever is used advantageously to axially displace the escapement lever. The position of the cam disk can be made adjustable by means of a dial, or similar actuating part, on the outside surface of the housing and it can be secured by a suitable click-stop device. A user of the infusion mechanism by moving the dial may personally select the infusion time and, without difficulty, shift to a different time cycle without interrupting the infusion process.

Another advantageous improvement provided by the invention consists in guiding the gear rack on a pair of rods fastened to a rocker arm which has one end pivotably connected to the housing. The other end of the rocker arm is operatively engaged with a traction spring and a cam disk 35 mounted on the coil spring winding shaft. As a result, when the cover is pivoted open the gear rack, which forces the syringe piston forward, is automatically disengaged from the feed mechanism. The rack is thereby rendered freely slidable and the syringe drive inoperative so that the syringe can be removed from the housing and be actuated again with the coil springs fully wound. Alternatively, the syringe can be deaerated or be actuated manually with the housing open to position the piston at a different location. The clockwork can unwind with the syringe placed in the apparatus and the cover open, without the syringe being actuated, because the feed mechanism is disengaged.

According to the invention, movement of the housing cover incorporates three important functions, namely, winding of both coil springs, a safety against closing the cover before the springs are completely wound and disengagement of the piston feed mechanism with the cover open.

The invention will be described further in conjunction with the attached drawings, in which:

FIG. 2 is a view of the apparatus shown in FIG. 1, with the housing cover and top removed to illustrate the feed mechanism, taken along the line II—II;

FIG. 3 is a view in the direction of arrow A in FIG. 2 and shows the feed mechanism and clockwork;

FIG. 3a is a view of the mechanism for engaging and disengaging the gear rack from the feed drive mechanism;

FIG. 4 illustrates the escape wheel engaged with part of the escapement lever on an enlarged scale;

FIG. 5 is an end view into the housing seen in the direction of the arrow B in FIG. 3;

FIG. 6 is a sectional view taken along the line VI—VI of FIG. 5;

FIG. 7 shows in exploded form the coil spring winding disks shown in FIG. 6; and FIG. 8 shows the middle disk of the disk arrangement shown in FIG. 7 in a different position and not blocked by ratchet 29.

Figure 1:
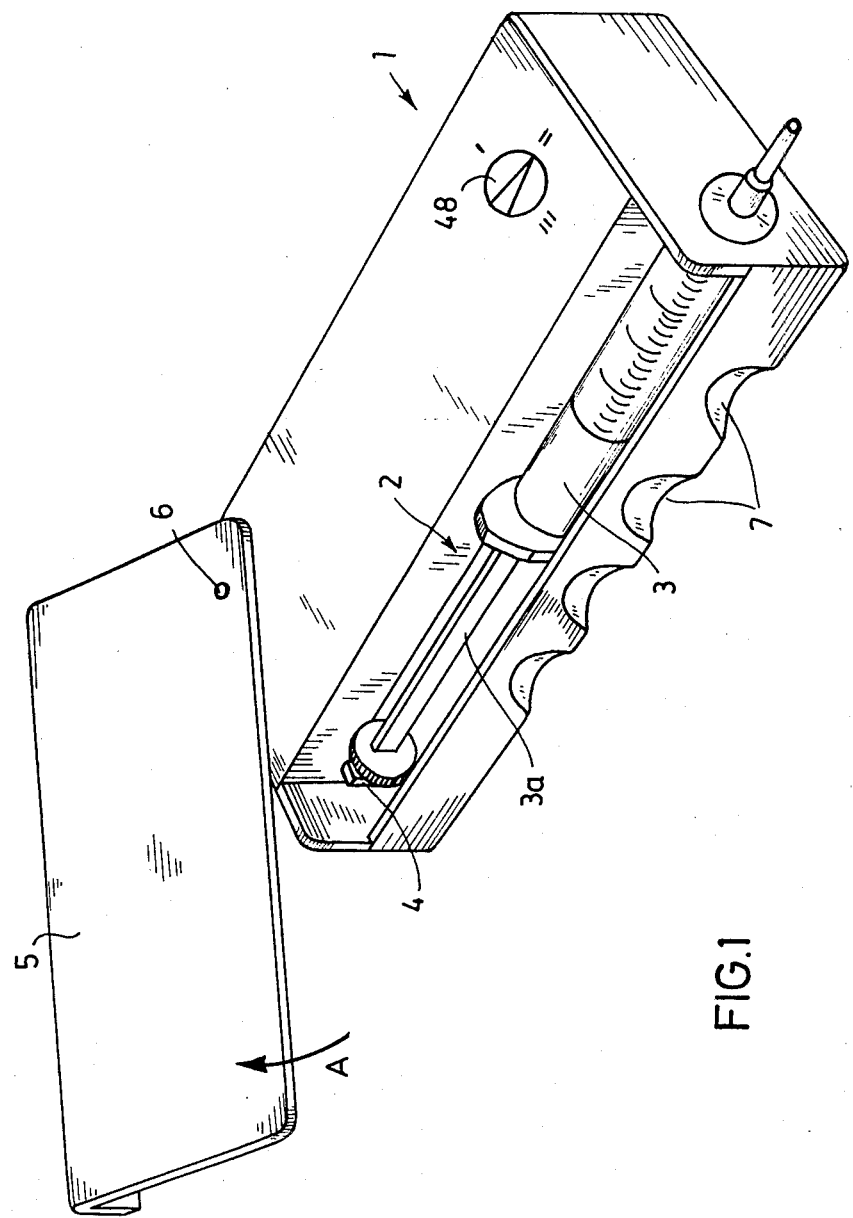
FIG. 1 illustrates diagrammatically one embodiment of apparatus with the injection syringe mounted in the apparatus in opened condition.

With reference to FIG. 1, the apparatus for continuous infusions comprises a housing 1 having a support 2 for an injection syringe, for example a disposal syringe. The support 2 is in a corner of the housing so it is open to the housing top and side. An arm 4 of a gear rack connectable to a feed drive extends into the syringe support 2 in the housing. The arm 4 presses against a piston 3A of injection syringe 3. Cover 5 is used to close the syringe support 2. The cover 5 is an angled plate pivotally mounted on the housing by shaft 6. The pivotal point of the cover 5 on shaft 6 is so arranged with respect to the housing that in all instances the front end, or plunger end, of the injection syringe 3 is released first when the cover 5 is pivoted in the direction of the arrow A for opening. Finger recesses 7 facilitate handling and operation of the apparatus.

The apparatus according to the invention is characterized by separate mechanical power means to drive the clockwork or timer and the feed mechanism. For this reason, the clockwork mechanism can be located on one side of a longitudinal central plane through the housing and the feed mechanism can be located on the other side of that longitudinal plane (FIG. 3).

In the embodiment illustrated by FIG. 3, the clockwork is located in the bottom space of the housing. In a conventional manner, the clockwork comprises a coil spring 8, the force of which is transmitted by a sprocket 18 on shaft 17, a minute (time) gear or wheel 9, a small minute or center gear or wheel 10 and a second (time) dual gear 11 (which has a small portion and a large portion) to a movement 12. The coil spring 8 is connected by a sprocket wheel 14 on shaft 17 and an index gear 15 with a spring winding shaft 13. The spring winding shaft 13 is joined to shaft 6 so that both shafts rotate simultaneously as a unit. Similarly, shaft 6 is connected to cover 5 so that they rotate together simultaneously. As a result, pivoting of the cover 5 winds the coil spring 8.

The spring winding shaft 13 also winds coil spring 16 associated with the feed mechanism and arranged on a shaft 17 coaxially to the coil spring 8. Both of the coil springs 8 and 16 are wound uniformly upon pivoting of cover 5. To assure that the cover 5 is always pivoted 180° so that both the coil springs 8 and 16 driving the clockwork and the feed mechanism respectively are always wound uniformly the cam and ratchet mechanism illustrated in FIGS. 6 to 8 is provided.

A helical and partly geared disk 19 is fixedly connected to cover 5 so that it rotates on shaft 6,13 when the cover is rotated. The helical shaped and partly geared disk 19 has a laterally positioned pin 20 which extends through an arcuate slot 21 in a second disk 22. Second disk 22 is only rotatable through a small angle alpha (FIG. 7). A circumferentially located radial recess 23 is provided in second disk 22. A third spiral disk 24, which is partly geared, is positioned coaxial to the two disks 19 and 22. An arcuate slot 25 is formed in disk 24 slightly longer than the arcuate slot 21 in disk 22. The pin 20 on disk 19 also extends into the slot 25. As the cover 5 is pivoted for winding the clockwork, the pin 20 rotates the disk 24 and its geared segment 26 transmits the pivoting movement of the cover 5 by sprocket wheel 28 (FIG. 3) to the shaft 17 bearing both spiral tension springs 8 and 16. Each time the cover 5 is pivotally opened, the cover is prevented from being returned to the closed position by the spring-loaded ratchet 29 which engages both the geared or toothed portion of disk 19 and the recess 23 in disk 22. The ratchet 29 is disengaged by the cam surface 30 of disk 22 only by pivoting the cover 180° and simultaneously but inherently completely winding both coil springs 8 and 16. Only after that is done can the cover be freely pivoted back into the housing closing position. The rotary movement of disk 22 through a small angle alpha (FIG. 7) is possible because the arcuate slot 25 in disk 24 is slightly longer than the arcuate slot 21 in disk 22.

The force exerted by the coil spring 16 of the feed mechanism is transmitted to sprocket 31 on shaft 17 which engages a drive transmission 32, shown in phantom in FIGS. 2 and 3, to escape wheel 50, sprocket 60, and, by additional elements of transmission 32, a pinion gear 33 which engages gear rack 34. Gear rack 34 has an arm 4 which presses against the end of piston or plunger 3A of injection syringe 3.

If the syringe 3 for any reason is to be removed prior to expiration of the total infusion time, the gear rack 34 can be disconnected until a syringe 3 is reinserted in syringe support 2 and the cover is closed. This can be done by automatically disengaging gear rack 34 from pinion gear 33 as cover 5 is pivoted open. The device illustrated in FIG. 3a performs this function. Cam 35 is connected to rotate with shaft 6,13 so that when cover 5 is pivoted cam 35 turns. Cam 35 presses on bow spring 36, or the like, which in turn presses on rocker arm 37 which supports gear rack 34. One end of rocker arm 37 is connected by pivot 38 (FIG. 2) to the housing 1. The other end of rocker arm 37 is connected to helical spring 39 which is connected at 40 to housing 1 (FIG. 3a). The rack 34 is guided by two rods 41, only one of which is illustrated in FIG. 2, and the ends of the rods 41 are fastened to the rocker arm 37. When the cover 5 is closed the mechanism is positioned as shown in FIG. 3a. When the cut-off portion of cam 35 presses on bow spring 36 the downward pressure on rocker arm 37 so applied is insufficient to overcome the tension applied by spring 39 pulling up the rocker arm. As a result the pinion gear 33 of the drive mechanism remains in engagement with the gear rack 34. When the cover 5 is opened the cam 35 rotates automatically and the higher rounded edge of the cam presses against bow spring 36. The higher force thereby applied by bow spring 36 to rocker arm 37 overcomes the force of helical spring 39 so that the rocker arm 37 moves in the direction of arrow C in FIG. 3a. The gear rack 34 moves with the rocker arm causing it to become disengaged from pinion gear 33.

The engaged feed mechanism is controlled by the clockwork. The control mechanism includes an eccentric 411 on shaft 42 containing second (time) wheel 11. Fork 43 of escapement lever arm 44 engages eccentric 411. Escapement lever 44, positioned pivotably on shaft 45, has two stop dogs 46 in tandem on its lower arm.

The stop dogs 46 of the escapement lever 44 coact with the wings or paddles of escape wheel 50 (FIG. 4) which is connected via sprocket 60 and the transmission 32 with pinion gear 33 which drives gear rack 34.

By impeding the rotation of escape wheel 50 upon impact of a wing against a stop dog 46 of the escapement lever 44, the previous gear phase of the feed mechanism is stopped in each instance so that feed by the gear rack 34 is divided into a series of sequential uniform small increments with the clockwork controlling the mechanism rhythm.

To produce different feed rates, the escapement lever 44 is axially adjustable on shaft 45. Undulated curved disk 47 (FIGS. 2 and 3) is used for axial displacement of escapement lever 44. Disk 47 is rotatable manually from the outside of the housing 1 by actuating part 48. Disk 47 engages a transverse slot 49 in the shaft 45. When disk 47 rotates, it causes axial displacement of escapement lever 44 so that it can engage the wings, which are of different widths, of escape wheel 50.

In the embodiment shown in FIG. 4, the escape wheel 50 has four radially located wings positioned at 90° from adjacent wings. Some of the wings are of different width and, specifically, the wing 51 has one-half the width of wing 52 placed opposite the former, while the other two wings 53 are one-half as wide as wing 51. By adjusting the escapement lever 44 so that with a revolution of the second (time) wheel 11 all four wings 51-53 of escape wheel 50 are impeded by the escapement lever 44, the gear on which the escape wheel 50 is located is blocked four times per minute so that small feed advances result and complete displacement of the syringe plunger or piston is achieved in a twenty-four hour period. For a twelve hour feed, only every other wing (180°) is impeded so that twice as much forward feed advance results as when each wing at 90° is impeded. The entire stroke length is displaced in a twelve hour running time when stop dogs 46 engage wings 51 and 52. By adjusting to a six hour continuous infusion, the forward thrust is stopped only once per 380° and a six hour running time is obtained over a 40 mm thrust length or plunger displacement. In a six hour running time, only wing 52 is stopped by stop dogs 46.

While a feed cycle is proceeding, the feed rate can be changed to a different cycle by means of actuating dial 48. Thus, by switching dial 48 the feed can be changed, for example, from a twelve hour feed rate to a twenty-four hour or to a six hour feed rate.

If it becomes desirable because of different conditions to adjust the mechanism for different feed rates, the wings on escape wheel 50 may be modified in size, shape or number to obtain the desired result.

The clockwork gearing or wheel arrangement by which sprocket 18 drives shaft 42 to actuate eccentric 41 is shown in the drawings schematically since conventional transmission mechanisms and movements can be used for that purpose. This is also so with respect to the transmission mechanism 32 by which sprocket 31 transmits power to escape wheel 50 and from it to pinion gear 33.

The foregoing detailed description has been given for clearness of understanding only, and no unnecessary limitations should be understood therefrom, as modifications will be obvious to those skilled in the art.

What is claimed is:

1. In an apparatus for continuous infusion of a liquid from an injection syringe having a plunger, a spring driven mechanism for advancing the syringe piston and a mechanical clockwork for controlling the piston advance, the improvement comprising a piston drive mechanism actuated by a first spring and wheel transmission and a clockwork control operated by a second spring and wheel transmission.

2. The improved apparatus according to claim 1 in which both springs are mounted coaxially on one spring shaft.

3. The improved apparatus according to claim 2 having a housing, a syringe support in the housing, a pivotable cover for the syringe support, means connecting the pivotable cover to a spring winding shaft so that they pivot together, and said spring shaft being operatively engaged to the spring winding shaft.

4. The improved apparatus according to claim 3 including a helical toothed disk fixedly connected to rotate with the cover and coacting with a ratchet in such a manner that the cover is lockable only after being pivoted about 180° from a closed position.

5. The improved apparatus according to claim 4 including a cam disk operably engaged by the helical toothed disk to disengage the ratchet when the cover is in a terminal pivotal position.

6. The improved apparatus according to claim 1 in which an eccentric is positioned on a shaft holding a second wheel of the clockwork, a shaft having an escape wheel, an escapement lever operably engaged by the eccentric to act on the escape wheel, a sprocket on the escape wheel shaft, transmission means driven by the sprocket, and a gear rack driven by the transmission means which advances a syringe piston.

7. The improved apparatus according to claim 6 in which the escape wheel has symmetrically arranged radial wings.

8. The improved apparatus according to claim 7 in which the escape wheel has four wings at 90° from each adjacent wing.

9. The improved apparatus according to claim 7 in which the escapement lever has two stop dogs in tandem which engage the escape wheel.

10. The improved apparatus according to claim 7 in which some of the wings are of unequal width and the escapement lever is axially movable on a shaft for selective engagement with escape wheel wings of different width.

11. The improved apparatus according to claim 10 including a rotatably mounted cam disk with undulated sides operably engaging the escapement lever to move it axially by rotation of the cam disk.

12. The improved apparatus according to claim 11 in which the cam disk with undulating sides is rotatable by a means outside of the housing which is secured by a click-stop device.

13. The improved apparatus according to claim 1 having a gear rack, for advancing the syringe piston, mounted on a pair of rods fastened to a rocker arm connected at one end to the housing.

14. The improved apparatus according to claim 13 in which the other end of the rocker arm is spring biased to engage the gear rack with the feed drive mechanism with the cover closed and to disengage the gear rack therefrom when the cover is open.

15. The improved apparatus according to claim 14 including a cam connected to a shaft rotatable with pivotal movement of the cover, and means displaceable by the cam to move the rocker arm so that the gear rack thereon disengages from the drive mechanism.

16. The improved apparatus according to claim 2 in which the springs are coil springs.

17. The improved apparatus according to claim 2 in which a spring shaft is operatively engaged to a spring winding shaft.

* * * * *